United States Patent [19]

Zardi

[11] Patent Number: 4,952,375
[45] Date of Patent: Aug. 28, 1990

[54] SYSTEM FOR REDUCING ENERGY CONSUMPTION IMPROVING REACTORS FOR HETEROGENEOUS CATALYTIC SYNTHESIS AND RELATED REACTORS

[75] Inventor: Umberto Zardi, Via Lucino 57, CH - 6932 Breganzona, Switzerland

[73] Assignees: Ammonia Casale S.A.; Umberto Zardi, both of Switzerland

[21] Appl. No.: 210,868

[22] Filed: Jun. 24, 1988

Related U.S. Application Data

[62] Division of Ser. No. 859,044, May 2, 1986, Pat. No. 4,755,362.

[30] Foreign Application Priority Data

May 17, 1985 [CH] Switzerland ............... 02100/85
Jul. 25, 1985 [CH] Switzerland ............... 03238/85

[51] Int. Cl.⁵ .................. B01J 8/04; C01C 1/04
[52] U.S. Cl. .................. 422/148; 422/191;
422/193; 422/198; 422/203; 423/360; 423/361
[58] Field of Search ........... 422/148, 191, 193, 198, 422/203; 423/360, 361

[56] References Cited

U.S. PATENT DOCUMENTS

| 3,372,988 | 3/1968 | Hanson | 23/198 |
|---|---|---|---|
| 3,918,918 | 11/1975 | Kahn et al. | |
| 4,101,281 | 7/1978 | Pagani | 23/288 |
| 4,181,701 | 1/1980 | Topsoe et al. | 422/158 |
| 4,230,669 | 10/1980 | Eagle et al. | 422/148 |
| 4,230,680 | 10/1980 | Becker et al. | 423/360 |
| 4,346,060 | 8/1982 | Eagle et al. | 422/148 |
| 4,518,574 | 5/1985 | Osman et al. | 423/360 |
| 4,594,227 | 6/1986 | Ohsaki et al. | 422/148 |

FOREIGN PATENT DOCUMENTS

60-110328 6/1985 Japan .
1118750 7/1968 United Kingdom .
1204634 9/1970 United Kingdom .

OTHER PUBLICATIONS

"Modernize Your Ammonia Converter . . . " Ammonia Casale S.A.
"Continuing Success for Ammonia Casale in Converter Revamping".
British Sulphur Coporation's Fourth International Conference on Fertilizers, London, Jan. 19–21, 1981, Part I, Paper #9, pp. 174–175, 177–183, 187, 189 and 193, Paper #26, pp. 672–675.

*Primary Examiner*—Barry S. Richman
*Assistant Examiner*—Jill Johnston
*Attorney, Agent, or Firm*—Ostrolenk, Faber, Gerb & Soffen

[57] ABSTRACT

The energy consumption of conventional reactors for heterogeneous synthesis, e.g., ammonia synthesis and methanol synthesis, wherein the synthesis gas flows substantially axially through catalyst beds, is substantially reduced by inserting in at least one catalyst bed: two concentric cylindrical substantially perforated walls to laterally delimit the bed; a bottom closure between these walls; and optionally a diaphragm on top of the bed. Optionally also, a catalyst granulometry gradient may be employed in the upper part of the bed. An upper minor portion of at least one of the cylindrical walls may be unperforated. The synthesis gas now traverses the bed substantially radially.

5 Claims, 5 Drawing Sheets

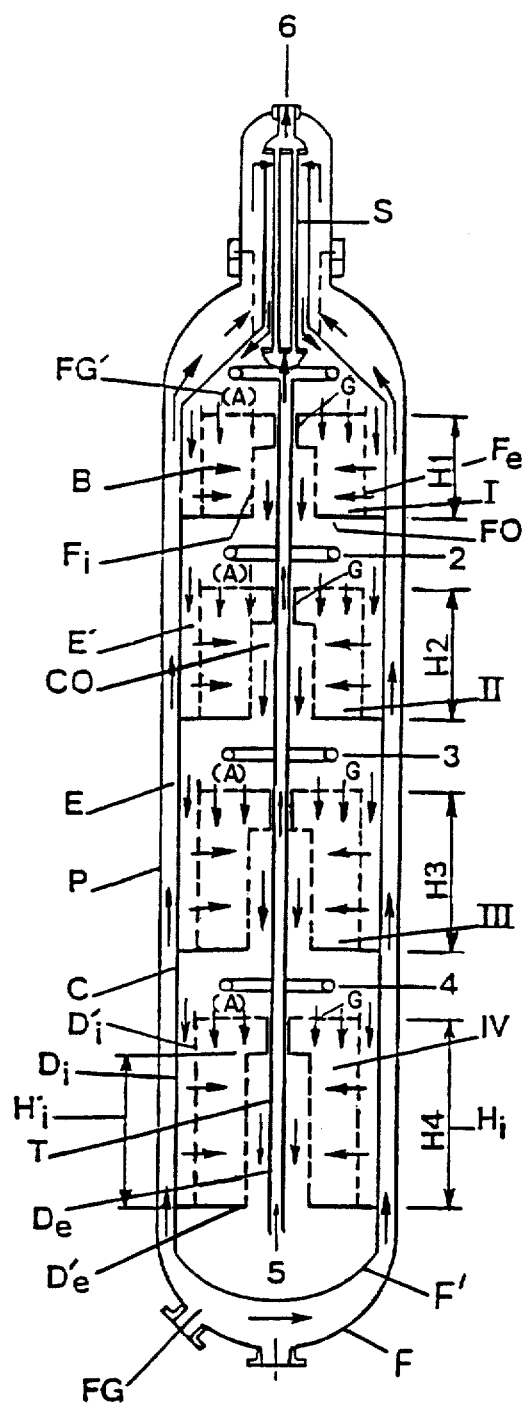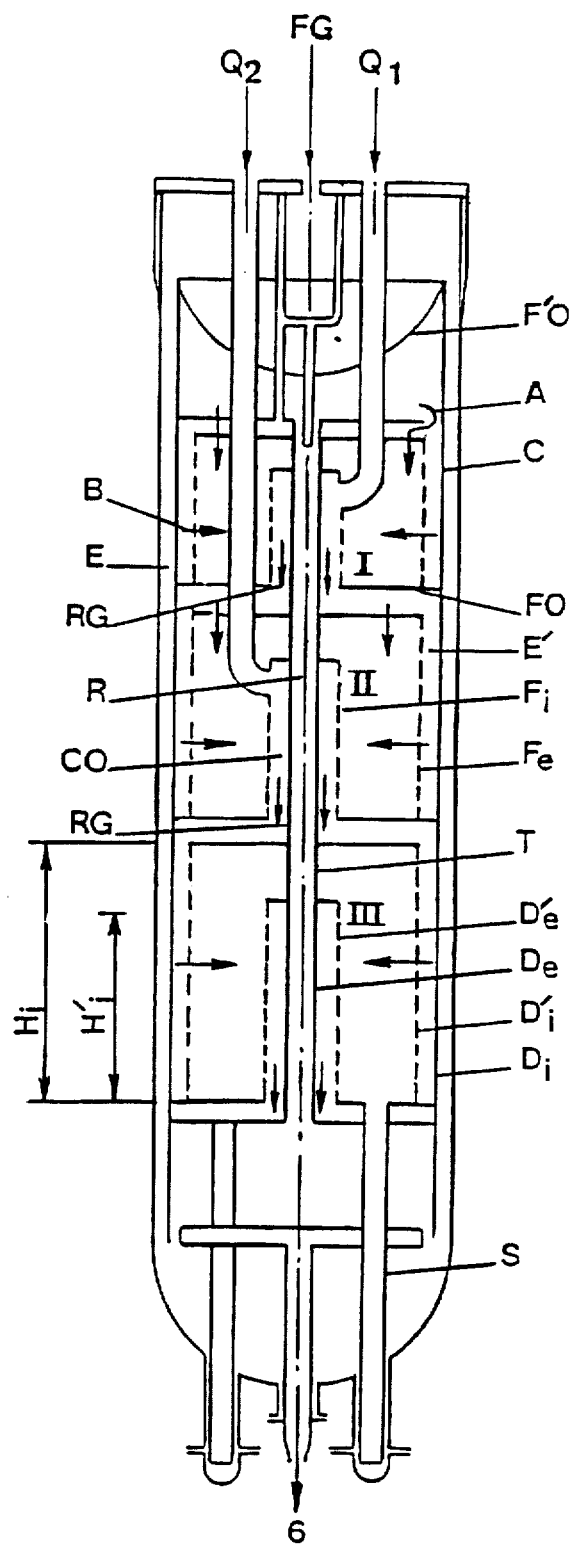
FIG. 2A
FIG. 2B

SYSTEM FOR REDUCING ENERGY CONSUMPTION IMPROVING REACTORS FOR HETEROGENEOUS CATALYTIC SYNTHESIS AND RELATED REACTORS

This is a division of application Ser. No. 859,044, filed May 2, 1986, now U.S. Pat. No. 4,755,362.

BACKGROUND OF THE INVENTION

1. Field of the Invention

The present invention is related to a system for increasing the conversion yield and reducing energy consumption in heterogeneous synthesis reactors, in particular for ammonia synthesis. Such reactors conventionally consist of an external shell, usually formed of a single piece, and of an internal cartridge which contains granular catalyst set in one or more catalyst beds arranged between an external cylindrical wall formed of parts of the cartridge, an internal cylindrical wall formed of parts of an internal transfer pipe for fresh synthesis gas, and a perforated bottom, the upper cross section of each bed being open and fed by the synthesis gas in an axial flow.

2. Description of the Prior Art

It is known that catalytic synthesis reactors under pressure, in particular for catalytic synthesis of ammonia, methanol, higher alcohols, etc., consist of an external shell, usually formed of a single piece, and of an internal cartridge containing catalyst granules of different forms and characteristics arranged in one or more layers (catalyst beds).

To obtain optimal temperatures in the various catalyst beds with exothermic reactions, the synthesis gas that flows through the various catalytic beds is usually cooled between beds, by means of fresh gas injection (quench reactor) or by direct interchange with the inlet cold gas.

Recently, proposals have been made for reactors with radial flow of the gas in the catalytic beds (U.S. Pat. Nos. 3,918,918 and 4,181,701, and European Patent Appln. No. 007743-A1, assigned to Lummus, Topsoe and Kellogg, respectively) or axial-radial (U.S. Pat. Nos. 4,372,920 and 4,405,562, assigned to the present assignee Ammonia Casale) which constitute great progress as compared with axial flow reactors, in particular when considerable amounts of catalyst are involved, by reducing pressure drops through the catalytic beds and, consequently, reducing energy consumption.

Axial gas flow required the use of reactors developed widthwise (low height-diameter ratio of the apparatus) with high costs of the equipment and high energy consumption.

The Ammonia Casale U.S. Pat. Nos. 4,372,920 and 4,405,562 have allowed the design of greatly simplified synthesis reactor cartridges with an internal structure having easy access for maintenance and for loading and unloading the catalyst and, at the same time, ensuring low pressure drops.

According to the above-mentioned patents, each catalyst bed is provided with a basket composed of an external perforated cylindrical wall, an internal perforated cylindrical wall and only one sealed bottom (the upper part of the basket is completely open); an upper part of at least one of said cylindrical walls being unperforated, the upper ends of said two cylindrical walls being on a plane approximately perpendicular to the longitudinal axis of said perforated walls. These walls form a zone where a minor portion of the gas runs through the catalyst bed in a prevalently axial flow, while the remaining major portion of the gas runs in a radial flow through the major part of the catalytic bed located between the perforated parts of the cylindrical walls of the bed.

Accordingly, the gas portion that runs through the bed in a prevalently axial flow is controlled exclusively by the height of the unperforated upper portion of at least one of said walls, said unperforated portion being only a minor part of the total height of the same wall(s).

Reactors whose dimensions correspond to a height-diameter ratio higher than 10 (i.e. diameter-height ratio less than 0.1) are especially suitable for the above-described technique.

In today's world economic situation, great importance is being given to the market of existing plant modernization. Most existing plants for the synthesis process (e.g. ammonia synthesis) employ reactors with axial flow in the catalytic beds (axial reactors) characterized by a low height-diameter ratio of the apparatus, owing to the above-mentioned requirement to minimize the pressure drops in the reactor. These conventional axial flow reactors have a high energy consumption and other drawbacks which are particularly burdensome when the reactors, as for instance those of the "lozenge" type, use only one catalytic bed which is very high, thus causing heavy pressure drops or energy consumption and strong buckling in the lower layers of the catalyst, which are therefore damaged and lose a portion of their activity.

SUMMARY OF THE INVENTION

The main object of the present invention is a system for reducing energy consumption of reactors for heterogeneous catalytic synthesis under pressure, in particular, of conventional axial reactors; this system is particularly suitable for application in the modernization of reactors by retrofitting reactors with axial gas flow, especially those with low height/diameter ratios like Kellogg and ICI reactors. Said conventional reactors are used in numerous high capacity plants (800-1500 TD) built mainly in the late seventies. The main characteristics of said plants, besides their high capacities, is the use of centrifugal gas compressors operated by steam produced in the plant according to an integrated cycle, and the use of the above-mentioned low efficiency axial reactors.

The above-mentioned plants are characterized by their high energy consumption which did not represent such a critical factor in the years when energy was available at a low cost, the axial type reactors being one of the causes of high consumption.

According to the present invention, it has surprisingly been found that conventional energy consuming axial reactors, especially those with a low height-diameter ratio, can be modified in an extremely easy and advantageous way, by restructuring their catalyst containing cartridge so that the axial gas flow is replaced by a substantially radial, preferably an axial-radial, or radial gas flow, in at least part of the catalytic beds, said gas flow being directed inwardly or outwardly.

Therefore, as mentioned in the introductory part of the description, the invention is related to a system characterized by modifying the catalytic beds by the following steps and measures:

(a) inside and near the cartridge (C) external wall, a cylindrical wall (Fe) is inserted which is substantially perforated on its height (Hi) and has a diameter (D'i) smaller than the internal diameter (Di) of the cartridge (C);

(b) an internal cylinder wall is also inserted which is also substantially perforated on the height (Hi) of the catalytic bed, and has a larger diameter than that (De) of the internal transfer pipe (T), and (c) a sealed annular bottom (F') is applied in the lower end (F) of the catalytic bed, which closes the annular space between (Di) and (D'e).

According to an embodiment of the invention, a minor portion (H-H'i) of at least one of said two inserted walls (Fe and/or Fi) is unperforated whereby the synthesis gas flows substantially radially (axial-radial flow, inwardly or outwardly) through said modified catalyst beds.

Preferably, the synthesis gas that flows axially through the upper open section of beds, modified according to the above embodiment, is divided into a major radial flow through the perforated height (H'i) of at least one wall (Fe and/or Fi) and a minor axial flow through the unperforated height (Hi-H'i).

One of the differences over the above-cited Ammonia Casale patents is that the gas portion that crosses in a predominantly axial flow in the modified catalytic beds according to the above embodiment is generally higher (even if major heights are considered for the unperforated upper part of the perforated cylindrical walls of the bed), while the gas portion that crosses the remaining part of the catalytic bed arranged in the perforated zones of the cylindrical walls with radial flow is reduced.

In a first version of above the embodiment of the invention, the upper minor unperforated portion is on the internal wall and the synthesis gas, after crossing the catalytic bed, is collected in the annular zone situated between the transfer pipe (T) with diameter (De) and the part of the internal wall (Fi) having height (H'i) and diameter (D'e).

In a second version, the upper minor unperforated portion is on the external wall (Fe) whose major perforated portion forms a channel for the reacted gas with the internal surface of the cartridge.

The ratio of the above-mentioned gas flows (the axial flow and the radial flow) will be different in the various catalytic beds of the cartridge if the beds have different heights (different height-diameter ratios of the baskets) as in the case where the present invention is applied for the modification of the reactors of the so-called Kellogg type in which the height of the catalytic beds of the internal cartridge increases in the various beds.

According to an advantageous feature of the invention, in some of the modified beds the gas portion crossing axially the upper portion of the beds can be reduced down to zero by using an upper flow-regulating diaphragm to reduce the open section between the upper ends of the two inserted cylindrical walls of the beds, said diaphragm being provided with appropriate openings (holes, grooves, etc.) or being totally closed, and directly in contact with the upper surface of the catalyst bed. The cross-sections of such openings may increase radially from the inside of the outside of the bed (or vice versa for outward gas flow beds).

According to another feature of the invention, the partial reduction of the axial gas flow can be achieved by providing catalyst size gradients, for instance the upper zone of the catalytic bed consists of a catalyst layer much smaller in size than the catalyst layer of the lower zone through which the gas flows radially, the thickness of said catalyst layer decreasing from the inside to the outside of the bed in a radial direction (or vice versa for outward gas flow beds). According to a further feature of the invention, said diaphragm can be totally unperforated and set on the upper surface of the bed.

BRIEF DESCRIPTION OF THE DRAWINGS

The invention will be fully understood in light of the following description of several, preferred but not limiting, embodiments shown in the accompanying drawings wherein all the figures are schematic and show partial longitudinal cross sections of reactors:

FIG. 1B shows the prior art ICI type reactor;

FIGS. 2A and 2B show the conventional axial reactors of FIGS. 1A and 1B modified according to the invention into reactors with substantially radial inwardly directed flow;

DETAILED DESCRIPTION OF THE PREFERRED EMBODIMENT

Figure 1A:
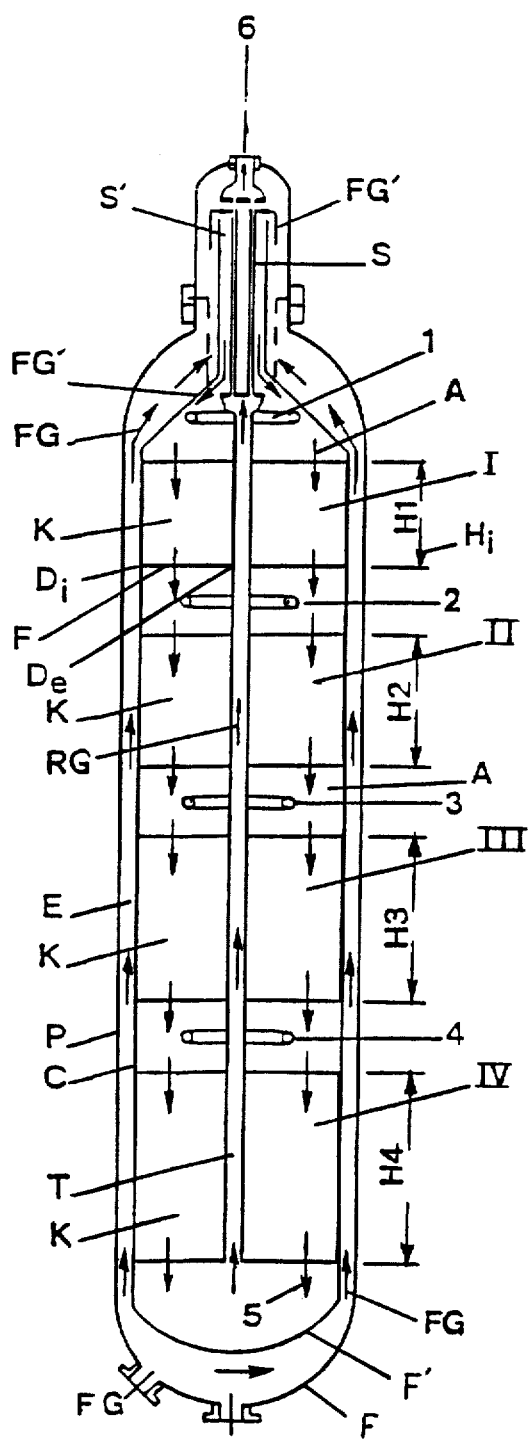
FIG. 1A shows the prior art Kellogg type reactor and FIG. 1B shows the prior art ICI type reactor.
Figure 1B:
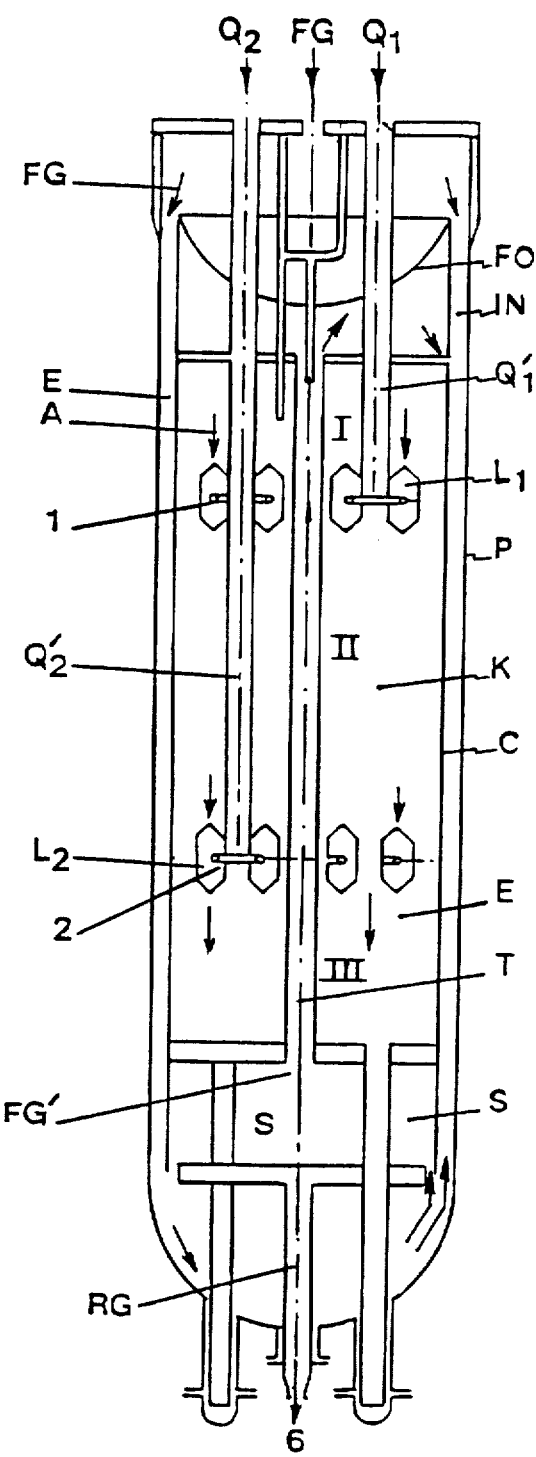

FIG. 1A shows schematically a conventional Kellogg type reactor having four catalyst beds, from I to IV, with the synthesis gas FG always in axial flow (arrows A) and with four quench injectors, from 1 to 4, of cooling gas at the top of each bed I-IV. FIG. 1B shows the so-called ICI type reactor with one catalyst bed divided into three sections I, II and III by two quench lozenges $L_1$ and $L_2$. In these and in all other figures, the reference letters and numbers indicate, respectively:

P is the outer pressure-resisting shell; C is the internal cartridge; E is the channel between the inner surface of shell P and the outer wall of cartridge C, said channel being generally traversed by the cold reaction gas FG to cool the shell surface; K indicates the generic catalyst in a generic basket from I to IV in FIG. 1, and from I to III in FIG. 2, each basket having for instance in FIG. 1 a height $H_1$, $H_2$, $H_3$ or $H_4$ and an outer diameter Di substantially equal to the internal diameter of cartridge C, and an inner diameter De substantially equal to the diameter of the central gas transfer pipe T; and a perforated bottom F. S indicates an indirect heat exchanger and 6 the reacted gas output.

In the conventional axial reactor, for instance of the Kellogg type shown in FIG. 1A, the fresh reaction gas FG enters through the bottom of the reactor (flow FG), flows upward in the space E between the shell P and the internal cartridge C, flows through the upper gas-gas heat exchangers, on the external surface of the exchanger (which is internally traversed by the hot reaction gas RG), is returned down through the annular passage S; is admixed with quench gas 1 and reaches the top of the first catalyst bed I (flow A), which is traversed entirely axially. Then the axial flow coming out of the bottom of the first bed I is admixed with quench gas 2 and enters and flows axially through the second bed II, at the bottom of which it is admixed with quench gas 3. This quenched flow enters and flows axially through bed III, is admixed with quench gas 4, penetrates and flows axially through bed IV, at the bottom of which it is collected as hot reacted gas 5, and enters central transfer tube T to go through the central top portion of the heat exchangers (where it exchanges heat with fresh gas FG') and goes out through outlet 6.

In FIG. 1B, another conventional entirely axial reactor is represented which differs from the reactor of FIG. 1A in that the quench gases $Q_1$ and $Q_2$ are introduced from the top of the reactor through tubes $Q_1$ and $Q_2$ respectively between the catalyst beds I, II and III by means of "lozenges" $L_1$ and $L_2$. This lozenge reactor is also known as ICI's lozenge reactor. The fresh gases FG are introduced from the reactor top, flow downwardly in channel E, enter as gas FG' the lower heat exchanger S, and are returned upwardly through transfer tube T at the exit of which they are directed downwardly as axial flow A through the catalyst layers. At the bottom of bed III, the reacted gas RG is taken out as flow 6. Further details of this known reactor are considered superfluous as they are very familiar to any person skilled in the art. Generally, said conventional reactors have a high pressure drop and thus are energy consumers; moreover, they use low efficiency large-size (6–10 mm) synthesis catalysts (K). The height $H_i$ of the various beds I, II and III and IV generally decreases from top to bottom (see FIG. 1A where $H_1 < H_2 < H_3 < H_4$).

The above-mentioned and other drawbacks are eliminated according to the invention by modifying the cartridge C and the therein contained catalyst baskets I, II, III and IV in order to have a substantially radial flow and to use a small-size catalyst (1.5–3 mm), which is more efficient than a large-size one keeping pressure drops reduced.

The new system is simply shown in FIGS. 2A and 2B where, according to the main feature of the invention, the old axial flow is changed (in this case in all beds) into a substantially radial flow, preferably and advantageously in a minor axial flow and in a major radial flow. To this end, each catalyst basket I, II, III, IV is deliminted by an internal substantially perforated wall $F_i$ having a diameter $D'_e$ larger than $D_e$ of the transfer tube (T) and an external substantially perforated wall $F_e$ having a diameter $D'_i$ lower than the internal diameter $D_i$ of the cartridge C. Moreover, each modified basket is provided with a closed bottom FO. In FIG. 2A, a first embodiment is shown in which the external wall $F_e$ is perforated on the entire height $H_i$ of the catalyst basket and has a constant diameter $D'_i$ along said height $H_{ei}$. The internal wall $F_i$ is perforated on a substantial portion $H'_i$ of $H_i$ and is unperforated on the remaining portion $H_i$-$H'_i$. The diameter $D'_e$ of $F_i$ is kept constant along the height $H'_i$ and reduced to the diameter $D_e$ of the transfer tube T on the height $H_i$-$H'_i$. Accordingly, a small portion of the preheated reaction gas FG' in each catalyst bed I, II, III and IV flows axially for the minor unperforated height $H_i$-$H'_i$ (where the internal wall $F_i$ is practically in contact with transfer tube T) and a main portion of the gas flows radially for the major perforated height or $H'_i$. In other words, the reaction gas is divided into a minor axial flow A and a major radial flow B. In FIGS. 2A and 2B, the radial flow B is inwardly, i.e. the fresh gas penetrates into the channel between the external wall $F_e$ (diameter $D'_i$) and the cartridge C (diameter $D_i$ slightly higher than $D'_i$) and because of the closed bottom FO on the entire annular portion $D'_e$-$D_i$, flows inwardly and is collected in the open space between the perforated portion $H'_i$ (diameter $D'_e$) and the transfer tube T (diameter $D_e$ slightly lower than $D'_e$). The annular portion contained between said diameters $D'_e$-$D_e$ is open, and both the axial and radial gas flows go out therethrough; from the first basket I they are admixed with quench gas 2 and flow again partly axially and partly radially through the second basket II and so on through the other baskets III and IV. The reacted gas leaving the last basket IV (indicated by 5) enters the transfer tube T, flows upwardly therein and leaves the top of the reactor in 6 (FIG. 2A, so-called Kellogg type reactor).

In FIG. 2B, the same steps are applied to a so-called ICI type reactor; the differences are that the quenches $Q_1$-$Q_2$ and the fresh synthesis gas FG here enter from the top of the rector, but the heat exchanger S and the associated exit 6 are at the bottom. Besides these minor differences, the system according to the invention utilizes here the same expedients as the reactor of FIG. 2A, i.e. an internal ($F_i$) and an external ($F_e$) substantially perforated wall, and a closed bottom FO are provided to form each catalyst basket I, II, III, the external wall $F_e$ having a constant diameter $D'_i$ on the entirely perforated height $H_i$ of the basket, while the internal wall $F_i$ has a diameter $D'_e$ on its major perforated height $H'_i$, and the diameter $D_e$ of the transfer tube T on the remaining unperforated height $H_i$-$H'_i$. Accordingly, the minor upper portion of the basket (having said height $H_i$-$H'_i$ and said smaller diameter $D_e$ of T) is unperforated and traversed by a minor axial gas flow while the majority entirely perforated portion of the basket having the height $H'_i$ and the annular width $D'_i$-$D'_e$ is traversed radially and inwardly by the major gas flow. The open channel E' between the inner cartridge surface (diameter $D_i$) and the external entirely perforated wall $F_e$ forms the passage for the radially inwardly directed still unreacted gas (flow B), while the shorter channel CO between the portion of the internal surface $F_i$ having diameter $D'_e$, and the transfer tube T having outer diameter $D_e$ acts as collector of the reacted gas flow RG, which radially and inwardly traverses the major catalyst basket height $H_i$-$H'_i$. The reacted gas RG coming out of the bottom of the last basket III flows through the heat exchanger S and leaves from 6.

Figure 3A:
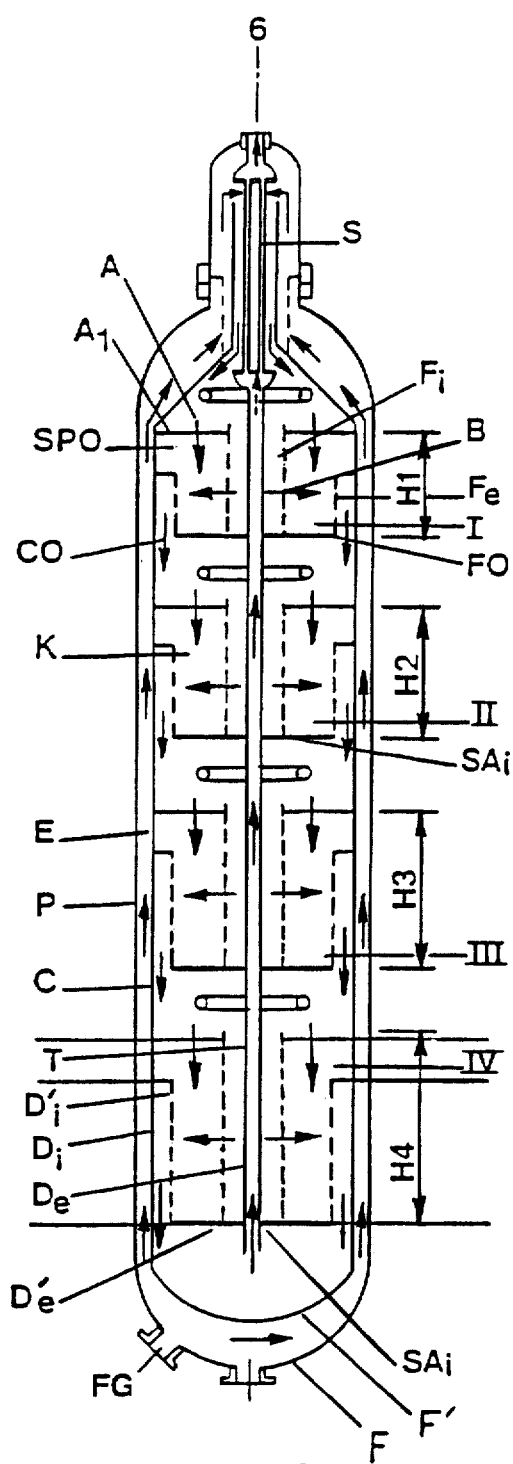
FIGS. 3A and 3B show reactors with substantially radial outwardly directed flow.
Figure 3B:
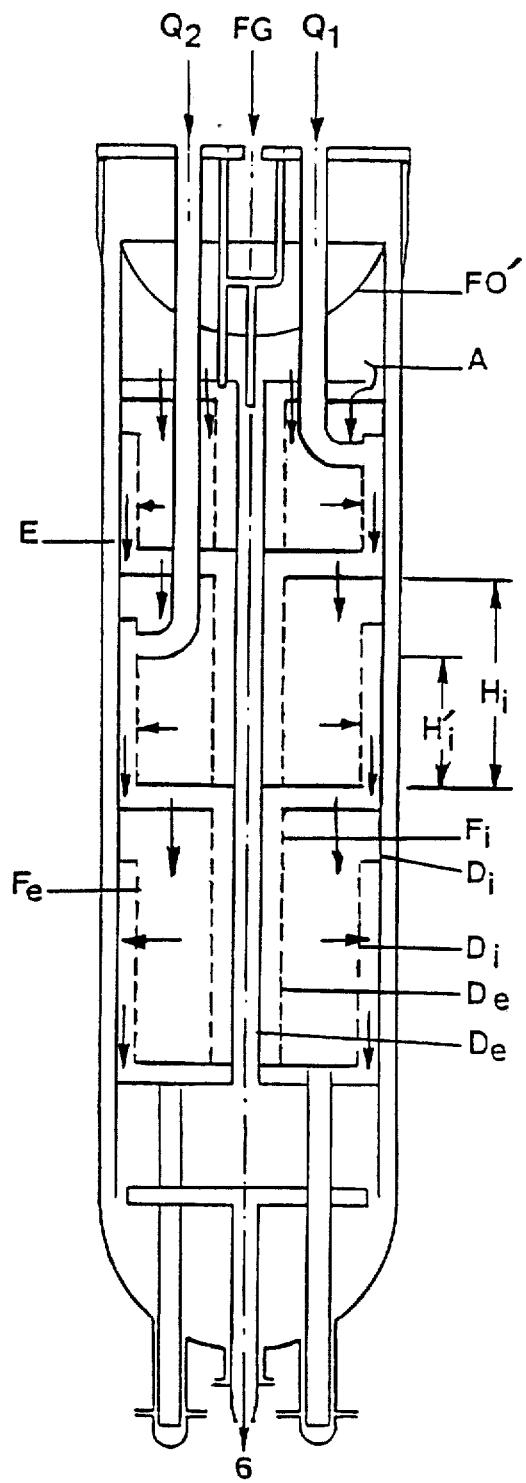

In FIGS. 3A and 3B, embodiments of outwardly directed flow is shown in which the internal wall $F_i$ is perforated on the total length $H_i$ and has a constant diameter $D'_e$ (slightly higher than the diameter $D_e$ of the internal transfer tube T), while the external wall $F_e$ is perforated on the height $H'_i$ having diameter $D'_i$ and is unperforated on the height $H_i$-$H'_i$ along which it takes the diameter $D_i$ of the cartridge C.

The lower closed bottom FO has now an annular width extending from the diameter $D_e$ of transfer tube T to the diameter $D'_i$ of the perforated height $H'_i$ of wall $F_e$. While in FIGS. 2A and 2B the bottom FO was sealed to the inner face of cartridge C, in the outward gas flow reactors of FIGS. 3A and 3B it is sealed to the outer surface of transfer tube T. In FIG. 3A, the annular sealing of the bottom FO to tube T is indicated by $SA_i$. As in FIG. 2A, the fresh gas FG enters the bottom, flows up in space E and then on the outer surface of the heat exchanger S, impinges axially the open upper face $A_1$ of the first catalyst basket I and flows axially on the portion $H_i$-$H'_i$ (indicated by SPO) (see flow A). Fresh gas FG penetrates also into the open channel between tube T and wall $F_i$ and flows outwardly radially (flow B) through the major lower portion $H'_i$ of each basket to be collected as reacted gas (flow CO) in the open space between the cartridge internal wall and the outer partially perforated wall $F_e$. The flow CO impinges again axially the next catalyst basket, flows through it axially on the minor portion SPO and then outwardly radially on the major portion $H_i$-$H'_i$ to be collected at the bottom of the reactor and outgoes through 6. In FIG. 3A, the heat exchanges S and gas outlet 6 are on top of the reactor, while in FIG. 3B heat exchanger S and outlet 6 are at the bottom.

Figure 4:
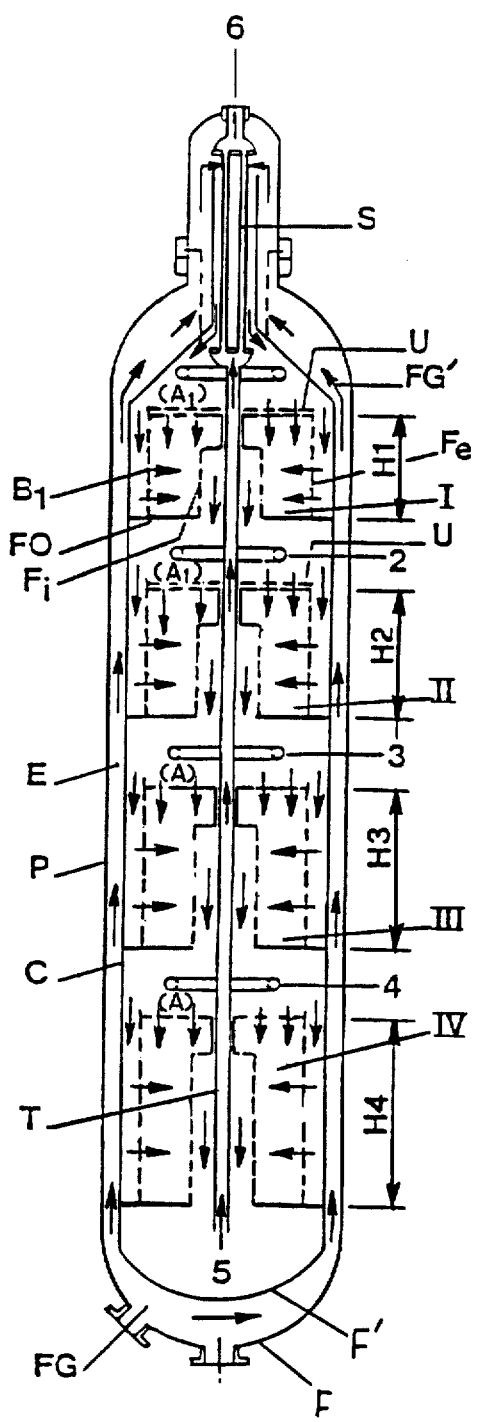
FIG. 4 is the inwardly radial reactor of FIG. 2A provided with flow regulators (diaphragms) on the top of the first two beds.

In FIG. 4 is shown a modification of the embodiment of FIG. 2A with, however, a flow regulator U (diaphragm) on the top open surfaces of the first two baskets I and II. Generally, the ratio of the axial/radial flows depends only on the ratio between the unperforated $H_i$-$H'_i$ and the perforated $H'_i$ heights. However, in this case in the upper two baskets the axial flows ($A_1$) are also regulated by the diaphragm U. Preferably, the axial flow regulator (reducer) is a diaphragm U. Preferably, the axial flow regulator (reducer) is a diaphragm having openings of different sizes and shapes, for instance holes which have different diameter which increases radially from the inside to the outside of the bed (or vice versa). The diaphragms may lie directly on the upper surfaces of the catalyst beds and the ratio of the axial to the radial flows in the various beds may be maintained substantially constant, preferably in the range of 0.02 to 0.2 (notwithstanding the difference in the heights $H_1$, $H_2$, $H_3$, $H_4$ of the various beds). Moreover, in place of or in addition to the diaphragms, a catalyst size gradient can be utilized. For instance, an upper granular layer much smaller in size than the lower layers of the bed may be used, the thickness of each catalyst layer decreasing, preferably from the inside of the outside of the bed, in radial direction (or vice versa). In another embodiment, in place of the perforated pressure reducing diaphragm, a closed diaphragm may be provided in some of the catalyst beds.

Figure 6:
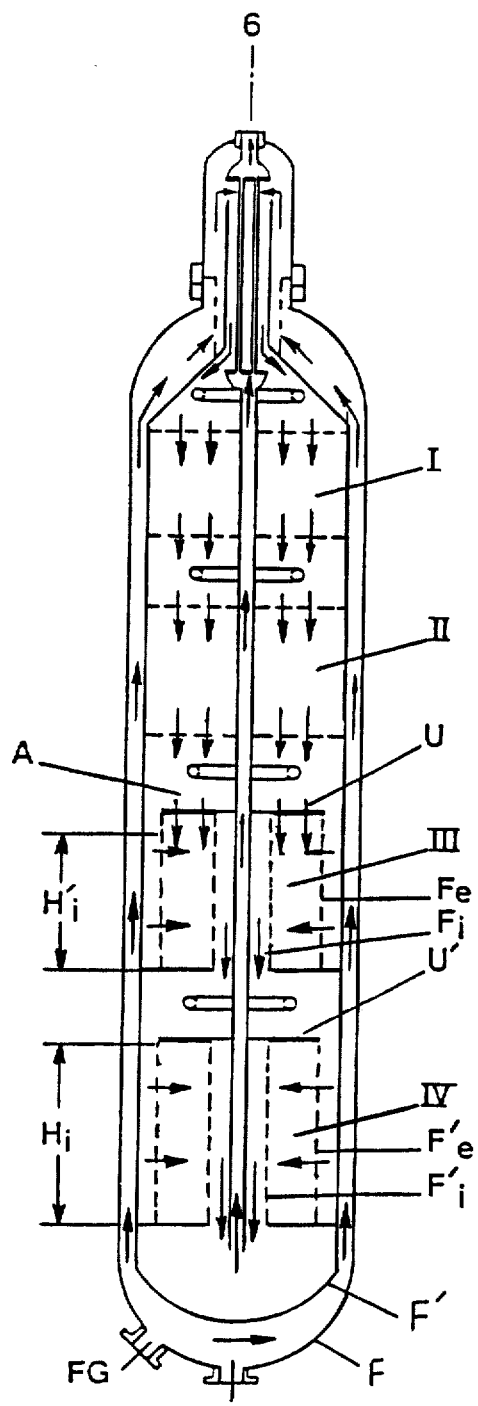
FIG. 6 is the inwardly radial reactor of FIG. 2A provided with closed diaphragms on the top of the last two beds.

FIG. 6 shows a particular embodiment in which at least one catalyst bed, e.g. two beds (I) and (II), are left unmodified, e.g., as in FIG. 1A (entirely axial flow), while at least a bed (e.g. III) is modified into an axial-radial flow bed having a partially open diaphragm U (as in FIG. 4), and at least one bed (e.g. IV) is transformed into an entirely radial flow basket by a diaphragm U' totally closed. In this last basket (IV), both walls $F'_e$ and $F'_i$ are perforated on their total height $H_i$ while in the basket III $F_e$ is perforated on the total height $H_i$ but $F_i$ has perforations only on $H'_i$. The unmodified axial flow bed(s) I and optionally II are those in the top portion of the reactor, i.e. the baskets with very low heights $H_1$ and $H_2$ (FIG. 1A) and this with very low pressure drops.

Figure 5:
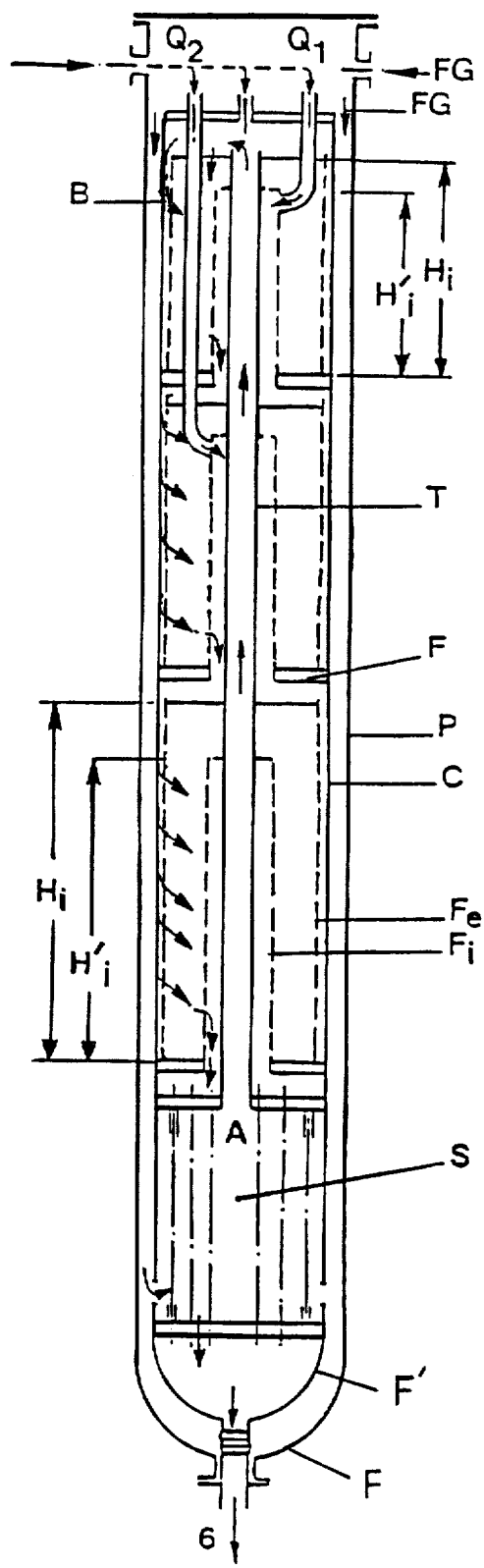
FIG. 5 shows the application of the invention in the modification of reactors having higher height/diameter ratios (e.g. ratios 10), for instance of the type TVA (Tennessee Valley Authority) and similar, and finally.

Finally, FIG. 5 shows that even if the system according to the invention is particularly advantageous on reactors with height/diameter ratios (H/D), less than 10, it can nevertheless be applied to reactors with ratios even higher than 10. The rector of FIG. 5 is of the so-called TVA (Tennessee Valley Authority) retrofitted according to the present invention and needs no further explanations.

The following non-limitative examples clarify some advantages of the invention.

EXAMPLE 1 (Comparison)

The typical performances that can be achieved by a Kellogg reactor of 4 adiabatic beds and 3 intermediate quenches, as shown in FIG. 1, are:

| capacity | 1090 MTD $NH_3$ |
|---|---|
| reactor inlet pressure | 155 bar abs |
| reactor outlet pressure (including quench) | 28378 Kmol/h |
| $NH_3$ content at reactor inlet | 2% mol |
| $NH_3$ content at reactor outlet | 12.58% mol |
| Reactor $\Delta P$ | 3.8 bar |
| other characteristics | |

| Bed # | Flow rate Kmol/h | $NH_3$ mol % | $H_2$ mol % | $N_2$ mol % | Inerts mol % | Temp. C. |
|---|---|---|---|---|---|---|
| 1 in | 16305.6 | 2.00 | 67.16 | 22.39 | 8.45 | 420.0 |
| 1 out | 15415.4 | 7.89 | 62.38 | 20.90 | 8.94 | 511.4 |
| 2 in | 19762.9 | 6.59 | 63.43 | 21.15 | 8.83 | 433.9 |
| 2 out | 19192.9 | 9.76 | 60.36 | 20.29 | 9.09 | 480.6 |
| 3 in | 23667.1 | 8.29 | 62.05 | 20.69 | 8.97 | 420.0 |
| 3 out | 23069.2 | 11.10 | 59.77 | 19.93 | 9.20 | 460.5 |
| 4 in | 26319.5 | 9.98 | 60.68 | 20.23 | 9.11 | 423.6 |
| 4 out | 25710.8 | 12.58 | 58.57 | 19.53 | 9.33 | 460.3 | quench gas temperature [C.] 138.0
quench after bed 1 flow rate [Kmol/h] 4347.46
quench after bed 2 flow rate [Kmol/h] 4474.25
quench after bed 3 flow rate [Kmol/h] 3250.35
Pressure [bar abs] 143.8

EXAMPLE 2

This example illustrates performance that can be achieved by the modified reactor according to the present invention (FIGS. 2A, 3A and 4).

The reactor cartridge has been modified so as to obtain an axial-radial reactor with 4 small-size (1.5–3 mm) catalyst beds and 3 intermediate quenches.

The performances can be resumed as follows:

| capacity | 1090 MTD $NH_3$ |
|---|---|
| reactor inlet pressure | 155 bar abs |
| reactor outlet pressure (including quench) | 22378 Kmol/h |
| $NH_3$ content at reactor inlet | 2% mol |
| $NH_3$ content at reactor outlet | 15.8% mol |
| Reactor $\Delta P$ | 1.8 bar |
| other characteristics | |

| Bed # | Flow rate Kmol/h | $NH_3$ mol % | $H_2$ mol % | $N_2$ mol % | Inerts mol % | Temp. C. |
|---|---|---|---|---|---|---|
| 1 in | 13168.4 | 2.00 | 67.16 | 22.39 | 8.45 | 340.0 |
| 1 out | 12121.4 | 10.81 | 60.00 | 20.01 | 9.18 | 473.7 |
| 2 in | 15398.8 | 8.93 | 61.53 | 20.51 | 9.02 | 407.0 |
| 2 out | 14808.2 | 13.29 | 58.00 | 19.34 | 9.38 | 468.4 |
| 3 in | 18105.0 | 11.23 | 59.67 | 19.89 | 9.21 | 413.0 |
| 3 out | 17549.0 | 14.75 | 56.30 | 18.94 | 9.51 | 461.4 |
| 4 in | 20184.8 | 13.09 | 58.16 | 19.39 | 9.37 | 423.0 |
| 4 out | 19711.6 | 15.80 | 55.95 | 18.65 | 9.59 | 459.5 | quench gas temperature [C.] 438.0
quench after bed 1 flow rate [Kmol/h] 3277.41
quench after bed 2 flow rate [Kmol/h] 3296.83
quench after bed 3 flow rate [Kmol/h] 2635.83
Pressure [bar abs] 145.8

EXAMPLE 3 (Comparison)

The typical performances that can be achieved by an ICI reactor having 3 adiabatic beds and 2 intermediate quenches as shown in FIG. 1B are:

| capacity | 1200 MTD $NH_3$ |
|---|---|

| -continued | |
|---|---|
| reactor inlet pressure | 238 bar abs |
| reactor inlet flow (quench included) | 28434 Kmol/h |
| NH₃ content at reactor inlet | 3% mol |
| NH₃ content at reactor outlet | 14.82% mol |
| reactor ΔP | 10 bar |
| quench gas temperature | 150° C. |

EXAMPLE 4

This example illustrates the performance of the reactor of Example 3 modified according of the invention (FIGS. 2B and 3B).

The reactor cartridge has been modified to obtain an axial-radial reactor with 3 layers of catalyst of small size (1.5-3 mm) with 2 intermediate quenches.

The performances can be summarized as follows:

| capacity | 1200 MTD NH₃ |
|---|---|
| reactor inlet pressure | 238 bar abs |
| reactor inlet flow (quench included) | 22884 Kmol/h |
| NH₃ content at reactor inlet | 3% mol |
| NH₃ content at reactor outlet | 18.16% mol |
| reactor ΔP | 2 bar |

What is claimed is:

1. A reactor for heterogeneous synthesis having perforated internal and external walls defining a plurality of catalyst beds within an outer shell, at least one said catalyst bed being provided with means for causing a synthesis gas to flow substantially axially in a minor zone and radially in a major zone, said means including a diaphragm positioned across the top of the internal and external walls and adapted to reduce the top open cross-section of each said bed.

2. A reactor according to claim 1, wherein said diaphragm is provided with holes and is placed on the upper surface of said catalyst bed itself, said diaphragm being adapted to maintain the ratio of axial gas flow to radial gas flow in the range of 0.02 to 0.2.

3. A reactor according to claim 2, wherein said holes increase in area in a direction extending radially outward across said catalyst bed.

4. A reactor according to claim 2, wherein said holes decrease in area in a direction extending radially outward across said catalyst bed.

5. A reactor according to claim 1, wherein at least one further catalyst bed of said plurality of catalyst beds includes a diaphragm adapted to reduce to zero the area of the open cross-section of said further catalyst bed.

* * * * *